United States Patent [19]

Gawne et al.

[11] Patent Number: 4,791,213

[45] Date of Patent: Dec. 13, 1988

[54] 2-HYDROXY-3-THIOXATHONYLOXY-1-PROPANAMINIUM SALTS

[75] Inventors: George Gawne, Great Bookham; Peter N. Green; William A. Green, both of Liverpool, all of England

[73] Assignee: Ward Blenkinsop & Company Limited, Cheshire, England

[21] Appl. No.: 927,018

[22] Filed: Nov. 5, 1986

[30] Foreign Application Priority Data

Nov. 29, 1985 [GB] United Kingdom ................ 8529448

[51] Int. Cl.[4] .......................................... C07D 335/16
[52] U.S. Cl. .......................................... 549/27; 522/53
[58] Field of Search ........................................ 549/27

[56] References Cited

U.S. PATENT DOCUMENTS

| | | | |
|---|---|---|---|
| 4,459,416 | 7/1984 | Curtis et al. | 549/27 |
| 4,505,794 | 3/1985 | Kvita et al. | 522/14 |
| 4,506,083 | 3/1985 | Kvita et al. | 549/27 |
| 4,602,097 | 7/1986 | Curtis | 549/27 |

FOREIGN PATENT DOCUMENTS

| | | | |
|---|---|---|---|
| 145016 | 11/1971 | Czechoslovakia | 549/26 |
| 0081280 | 6/1983 | European Pat. Off. | 549/27 |
| 1434486 | 5/1976 | United Kingdom | 546/18 |

Primary Examiner—Mary C. Lee
Assistant Examiner—Kurt G. Briscoe

[57] ABSTRACT

The invention provides thioxanthone derivatives of general formula

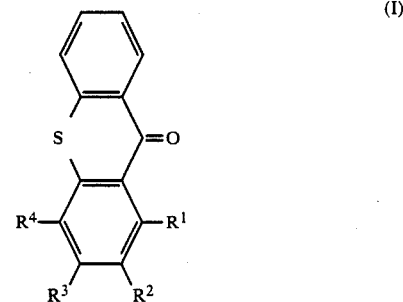

wherein one of $R^2$, $R^3$ and $R^4$ is a group of formula

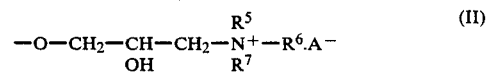

in which one of $R^5$, $R^6$ and $R^7$ is an alkyl or a benzyl group, the others being alkyl groups and $A^-$ represents an anion, and $R^1$ and the others of $R^2$, $R^3$, and $R^4$ are independently selected from hydrogen atoms, alkyl groups and alkoxy groups; and the use of such derivatives as photoinitiators, particularly in aqueous photopolymerizable compositions for the production of stencils for screen printing.

5 Claims, No Drawings

2-HYDROXY-3-THIOXATHONYLOXY-1-PROPANAMINIUM SALTS

This invention relates to thioxanthone derivatives, their preparation, photopolymerisable compositions containing them, use of such compositions in the production of stencils for screen printing, screens for screen printing coated with such compositions, and the use of thioxanthone derivatives as photoinitiators.

Three main photosensitive systems are used in screen printing, which are usually referred to as direct, indirect and direct/indirect methods. The prior art photoinitiators include certain dichromate compounds, polymeric diazonium salts and a leuco sulphuric acid ester of an indigo or thioindigo dye. When these photoinitiators are employed in any of the screen printing methods they suffer the disadvantage of being sparingly soluble in water so necessitating the addition of a solution of a peroxide or employment of large quantities of humectant or use of two pack systems.

In order to overcome these difficulties, EP-A-81280 discloses that certain thioxanthones contaning anionic groups such as carboxylic acid or sulphonic acid groups, have useful solubility in water of a suitable pH and can be used as photoinitiators in screen printing. These thioxanthones have the formula

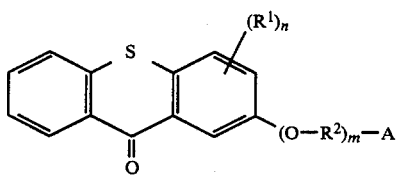

where $R^1$ is halogen, alkyl, alkoxy, alkylthio, nitro, amino, alkylamino, dialkylamino, hydroxyalkylamino, alkanoylamino, benzoylamino, N-alkanoyl-N-benzoylamino, sulphonamido or acetyl, $R^2$ is alkylene of 1 to 4 carbon atoms, n is 0, 1 or 2, m is 1 or 2, and A is —COOH, —SO$_3$H, —OSO$_3$H, or —OCO—X—COOH (where X is such that HOOC—X—COOH is a di- or tri-carboxylic acid of up to 8 carbon atoms), the aforesaid alkyl, alkoxy, and alkenyl residues containing up to 4 carbon atoms each, and water-soluble salts thereof.

There have now been discovered certain novel thioxanthone derivatives which are very water-soluble over a wide pH range.

According to the present invention there are provided thioxanthone derivatives of general formula

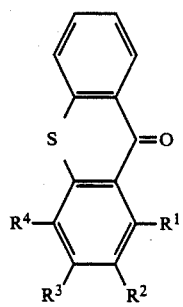

wherein one of $R^2$, $R^3$ and $R^4$ is a group of formula

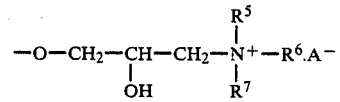

in which one of $R^5$, $R^6$ and $R^7$ is an alkyl or a benzyl group, the others being alkyl groups and $A^-$ represents an anion, and $R^1$ and the others of $R^2$, $R^3$, and $R^4$ are independently selected from hydrogen atoms, alkyl groups and alkoxy groups.

An alkyl or alkoxy group $R^1$, $R^2$, $R^3$ or $R^4$ is preferably a $C_{1-6}$ alkyl or $C_{1-6}$ alkoxy group, more preferably a $C_{1-4}$ alkyl or $C_{1-4}$ alkoxy (e.g. methoxy) group. In preferred embodiments of the invention, $R^1$ and said others of $R^2$, $R^3$ and $R^4$ are independently selected from hydrogen atoms and methyl groups.

It is preferred for one of $R^5$, $R^6$ and $R^7$ to be a $C_{1-20}$ alkyl group (e.g. a cetyl group) or a benzyl group, the others being $C_{1-6}$ alkyl, preferably $C_{1-4}$ alkyl groups. In preferred embodiments of the invention, $R^5$, $R^6$ and $R^7$ are all methyl groups.

$A^+$ may represent $\frac{1}{2}$ of a divalent anion, e.g. $\frac{1}{2}SO_4^{2+}$, but is preferably a monovalent anion e.g. a halide ion. A preferably represents a chlorine or bromine atom, and is very conveniently a chlorine atom.

Thioxanthone derivatives of formula I wherein $R^2$ or $R^4$ represents the group of formula II are preferred.

The invention further provides a process for the preparation of a thioxanthone derivative of formula I as defined above which comprises reacting a hydroxythioxanthone corresponding to formula I wherein in place of the group of formula II is a hydroxy group, with a compound of formula

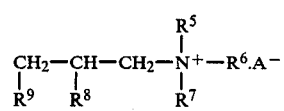

wherein $R^5$, $R^6$, $R^7$ and $A^-$ are all as defined for the group of formula II, $R^8$ is a group —OH and $R^9$ is a leaving group, or $R^8$ and $R^9$ together represent an oxygen atom, in the presence of a base.

A leaving group $R^9$ may conveniently be a halogen atom. Preferably when $R^8$ is a group —OH, $R^9$ is a chlorine atom.

The hydroxythioxanthones corresponding to formula I wherein in place of the group of formula II is a hydroxy group are either known compounds, preparable by known methods, or they may be prepared by methods analogous to known processes. Suitable methods will be apparent to those skilled in the art by reference to, for example, EP-A-81280; DE-A-2504642; Czechoslovakian Pat. No. 145,016; R. N. Sen and S. C. Sen Gupta, J. Ind. Chem. Soc., 1929, 6, 273; H. Christopher and S. Smiles, J.C.S., 1911, 99, 2050–1; and A. Mustafa and O. H. Hishmat, J.A.C.S., 1957, 79, 2227–8.

Reaction of the hydroxythioxanthone with the compound of formula III may conveniently be effected using an alkanol e.g. a $C_{1-3}$ alkanol, conveniently ethanol, or a polar aprotic solvent such as N,N-dimethylformamide as solvent, at temperatures in the range 60° C. to reflux temperature. Reaction at reflux temperature is very convenient. Convenient bases include alkali metal (e.g. sodium or potassium) alkoxides and hydroxides.

Further in accordance with the invention there is provided an aqueous photopolymerisable composition comprising an aqueous dispersion or solution of at least one polymerisable monomer and, as photoinitiator, a thioxanthone derivative of formula I. The invention also extends to the use of such a composition in the production of a stencil for screen printing, and to screens for screen printing coated with such a composition and dried.

Suitable such aqueous photopolymerisable compositions comprise compositions as described in EP-A-81280, substituting a thioxanthone derivative of formula I for the photoinitiator thioxanthone thereof. Accordingly the disclosure of EP-A-81280 is incorporated herein by reference.

The invention also comprises the use of a derivative of formula I as photoinitiator.

Compounds of formula I possess the property of having useful absorption of actinic light above 330 nm. In addition to their use a photoinitiators as described above in photopolymerisable compositions, they may also be employed in the manufacture of water based U.V. curable inks.

The invention will be further understood from the following Examples, of which Examples 1 to 6 relate to the preparation of compounds of formula I, and Example 7 demonstrates efficacy of the compounds as photoinitiators.

EXAMPLE 1

2-Hydroxy-3-(9-oxo-9H-thioxanthen-4-yloxy)-N,N,N-trimethylpropanaminium chloride 4-Hydroxythioxanthone (5.7 g) (mp 284.5° to 286.5° C., prepared by methods analogous to those of DE-A-2 504 642 and Czechoslovakian Pat. No. 145,016) and glycidyl trimethylammonium chloride (5.44 g, 70% assay) together with absolute ethanol (95 ml) were stirred and brought to reflux whereupon the pH was adjusted to ca. 9 by the addition of a few drops of ethanolic sodium ethoxide solution (3% w/v). After four minutes refluxing a clear solution resulted and after a further three hours refluxing a crystalline solid appeared. After refluxing for a further three and one half hours, water (7 mls) was added and the pH was adjusted to ca. 3 by the addition of a few drops of 2N isopropanolic hydrogen chloride. Hot filtration followed by ice bath cooling of the filtrate and filtration gave the crude title compound which was washed with isopropanol and dried in an air oven at 60° C. The dull pale green solid (8.58 g; mp 267° to 268° C.) was recrystallised from a mixture of ethanol (90 mls) and water (7 mls), washed with ethanol and dried, giving 2-hydroxy-3-(9-oxo-9H-thioxanthen-4-yloxy)-N,N,N-trimethyl-1-propanaminium chloride (7.03 g; 87.8%) as light green crystals, mp 268.5°-269.2° C.

Analysis: Calc. for $C_{19}H_{22}ClNO_3S$: 0.25$H_2O$; C 59.36; H 5.90; N 3.64; Cl 9.22; S 8.34. Found: C 59.53; H 5.76; N 3.63; Cl 9.48; S 8.40.

An aqueous solution of this compound has an absorption maximum at 391 nm with an E (1%; 1 cm) of 149.

EXAMPLE 2

2-Hydroxy-3-(1-methyl-9-oxo-9H-thioxanthen-4-yloxy)-N,N,N-trimethyl-1-propanaminium chloride 4-Hydroxy-1-methylthioxanthone (6.05 g), (prepared by a method analogous to that of R. N. Sen and S. C. Sen Gupta, J. Ind. Chem. Soc., 1929, 6, 2730) and glycidyl trimethylammonium chloride (5.44 g; 70% assay) together with absolute alcohol (60 mls) were stirred and brought to reflux whereupon the pH was adjusted to ca. 9 by the addition of a few drops of ethanolic sodium ethoxide solution (3% w/v). After two minutes refluxing a clear solution resulted and after a further two hours refluxing a crystalline solid appeared. This was redissolved by the addition of water (13 mls) and refluxing continued for an additional four hours. After adjusting the pH to ca. 4 by the addition of a few drops of 2N isopropanolic hydrogen chloride hot filtration followed by ice bath cooling of the filtrate and filtration gave the crude title compound which was washed with ethanol and vacuum dried.

The yellow solid (6.37 g; mp 269° to 270.5° C.) was recrystallised from ethanol containing a little water, washed with ethanol and dried in an air oven at 70° C. giving 2-hydroxy-3-(1-methyl-9-oxo-9H-thioxanthen-4-yloxy)-N,N,N-trimethyl-1-propanaminium chloride (4.5 g; 45.6%) as yellow crystals (mp 271° to 272° C.).

Analysis: Calc. for $C_{20}H_{24}ClNO_3S$: C 60.98; H 6.14; N 3.56; Cl 9.00; S 8.14. Found: C 60.70; H 6.15; N 3.48; Cl 9.01; S 8.13.

An aqueous solution of this compound has an absorption maximum at 390 nm with an E (1%; 1 cm) of 134.5.

EXAMPLE 3

2-Hydroxy-3-(9-oxo-9H-thioxanthen-2-yloxy)-N,N,N-trimethyl-1-propanaminium chloride Sodium (1.36 g) was reacted with absolute ethanol (120 mls) and 2-hydroxy-thioxanthone (11.4 g) (prepared by a method analogous to that of H. Christopher and S. Smiles. J.C.S., 1911, 99, 2050-2051) was added. To the stirred refluxing mixture (3-chloro-2-hydroxypropyl)trimethyl ammonium chloride (10.7 g) was added and the mixture refluxed overnight. After adjusting the pH to ca. 4 via the addition of a few drops of 2N isopropanolic hydrogen chloride solution, hot filtration followed by ice bath cooling of the filtrate and filtration gave the crude title compound which was washed with methanol and vacuum dried.

The yellow solid (15.3 g; mp 245° to 246.5° C.) was recrystallised from a mixture of ethanol (150 mls) and methanol (40 mls), washed with ethanol and vacuum dried giving 2-hydroxy-3-(9-oxo-9H-thioxanthen-2-yloxy)-N,N,N-trimethyl-1-propanaminium chloride (14.5 g; 72.8%) as yellow crystals, mp 245° to 246.5° C.

Analysis: Calc. for $C_{19}H_{22}ClNO_3S$: 1$H_2O$: C 57.35; H 6.08; N 3.52; Cl 8.91; S 8.06. Found: C 57.73; H 6.01; N 3.40; Cl 8.77; S 8.02.

An aqueous solution of this compound has an absorption maximum at 404 nm with an E (1%, 1 cm) of 135.

EXAMPLE 4

2-Hydroxy-3-(4-methyl-9-oxo-9H-thioxanthen-2-yloxy)-N,N,N-trimethyl-1-propanaminium chloride 2-Hydroxy-4-methylthioxanthone (6.5 g) (prepared by a method analogous to that of A. Mustafa and O. H. Hishmat, J.A.C.S., 1957, 79, 2227-8) and glycidyl trimethylammonium chloride (5.12 g; 80% assay) together with absolute alcohol (70 mls) were stirred and brought to reflux, whereupon the pH was adjusted to ca. 9 by the addition of a few drops of ethanolic sodium ethoxide solution (3% w/v). After two hours refluxing a clear solution resulted and after a further 18 hours reflux a crystalline solid appeared. Solution was effected by the addition of methanol (70 mls) followed by water (2 mls)

and the mixture was refluxed overnight. After adjusting the pH to ca. 4 by the addition of a few drops of 2N isopropanolic hydrogen chloride, hot filtration followed by ice bath cooling of the filtrate and subsequent filtration gave the crude title compound which was washed twice with ethanol and vacuum dried.

The yellow solid (9.6 g; mp 247° to 253° C.) was recrystallised from a mixture of ethanol (60 mls), methanol (60 mls) and water (6 mls), washed with ethanol and vacuum dried giving 2-hydroxy-3-(4-methyl-9-oxo-9H-thioxanthen-2-yloxy)-N,N,N-trimethyl-1-propanaminium chloride (8.0 g; 77.7%) as yellow crystals, mp 253.3° to 255° C.).

Analysis: Calc. $C_{20}H_{24}ClNO_3S$: $1H_2O$: C 58.33; H 6.36; N 3.40; Cl 8.61; S 7.78. Found: C 58.65; H 6.54; N 3.27; Cl 8.51; S 7.73.

An aqueous solution of this compound has an absorption maximum at 404 nm with an E (1%; 1 cm) of 144.

EXAMPLE 5

2-Hydroxy-3-(3,4-dimethyl-9-oxo-9H-thioxanthen-2-yloxy)-N,N,N-trimethyl-1-propanaminium chloride 2-Hydroxy-3,4-dimethylthioxanthone (mp 309°–310° C. after recrystallisation from 70% v/v dimethylformamide/water; microanalysis:-Calcd. for $C_{15}H_{12}O_2S$: C 70.30; H 4.72; S 12.51. Found C 70.22; H 4.73; S 12.37) was prepared by adding 2,3-dimethylphenol (24.4 g) during two hours to a stirred mixture of 2,2'-dithiobisbenzoic acid (15.3 g) and conc. sulphuric acid (150 mls) whilst the temperature was kept at 15°±5° C. via ice bath cooling. The temperature was then raised to 65° C. and maintained at 65°±5° C. for one hours after which the mixture was allowed to cool for 16 hours, before being quenched into water (500 mls) at 95°±5° C. and then stirred for thirty minutes prior to filtration. The residue was washed twice with water and then slurried in water (250 mls) at 70° C. and sodium bicarbonate (44 g) was slowly added until the pH became 8. After boiling for ten minutes the mixture was filtered and the residue washed sequentially with water (X3) then isopropanol (X1). Drying in an air oven at 60° C. gave crude 2-hydroxy-3,4-dimethylthioxanthone (18.59 g) as dull yellow crystalline solid, mp 298° to 302° C.

2-Hydroxy-3,4-dimethylthioxanthone (6.4 g) was dissolved in dimethylformamide (40 mls) at 104° C. and after hot filtration, glycidyltrimethylammonium chloride (5.44 g; 70% assay) as a slurry in dimethylformamide (10 mls) was aded to the filtrate at 100° C. The pH was adjusted to ca. 9 by the addition of a few drops of ethanolic sodium hydroxide solution (3% w/v) and after twelve minutes stirring at 100° C. a crystalline solid appeared. After a further six hours stirring at 100° C. the pH was adjusted to ca. 6 by the addition of a few drops of 2N isopropanolic hydrogen chloride and then the mixture was cooled in an ice bath. Filtration followed by sequential washing of the residue with dimethylformamide (X1) and isopropanol (X3) and then air drying at 70° C. gave 2-hydroxy-3-(3,4-dimethyl-9-oxo-9H-thioxanthen-2-yloxy)-N,N,N-trimethyl-1-propanaminium chloride (7.57 g; 72.4%) as a pale yellow solid, mp 271.5° to 273.5° C.

Analysis: Calc. for $C_{21}H_{26}ClNO_3$: $0.75H_2O$. C 59.82; H 6.58; N 3.36; Cl 8.41; S 7.61. Found: C 59.90; H 6.55; N 3.23; Cl 8.43; S 7.69.

An aqueous solution of this compound has an absorption maximum at 402 nm with an E (1%; 1 cm) of 115.

EXAMPLE 6

2-Hydroxy-3-(1,3,4-trimethyl-9-oxo-9H-thioxanthen-2-yloxy)-N,N,N-trimethyl-1-propanaminium chloride 2-Hydroxy-1,3,4-trimethylthioxanthone was prepared by adding 2,3,6-trimethylphenol (18.6 g) during two hours to a stirred mixture of 2,2'-dithiobisbenzoic acid (30.6 g) and conc. sulphuric acid (300 mls) whilst the temperature was kept at 12.5°±2.5° C. via ice bath cooling. After heating at 75°±5° C. for one hour the mixture was cooled to 50° C. prior to stirring into hot water (2 liters). Filtration, followed by water washing and drying in an air oven at 70° C. gave the crude product which was recrystallised from a mixture of dimethylformamide (140 mls) and water (60 mls). Filtration followed by washing ($H_2O$) and drying at 70° C. gave 2-hydroxy-1,3,4-trimethylthioxanthone (38.4 g; 71.1%) as khaki crystals, mp 201° to 204° C.

2-Hydroxy-1,3,4-trimethylthioxanthone (6.75 g) and glycidyltrimethylammonium chloride (6.44; 70% assay) together with absolute alcohol (60 mls) were stirred and brought to reflux whereupon the pH was adjusted to ca. 9 via the addition of a few drops of ethanolic sodium ethoxide solution (3% w/v). After refluxing for one hour a clear solution resulted. The mixture was refluxed for 16 hours and methanol (30 mls) plus water (2 mls) were added to effect homogenity. After adjusting the pH to ca. 3 by the addition of a few drops of 2N isopropanolic hydrogen chloride solution hot filtration followed by ice bath cooling of the filtrate and subsequent filtration gave the crude title compound which was washed thrice with ethanol and vacuum dried. The fawn solid (9.21 g; mp 258.5° to 260.5° C.) was recrystalised from a mixture of ethanol (75 mls) and methanol (90 mls), washed with ethanol and vacuum dried giving 2-hydroxy-3-(1,3,4-trimethyl-9-oxo-9H-thioxanthen-2-yloxy)-N,N,N-trimethyl-propanaminium chloride (6.5 g, 61.0%) as fawn crystals, mp 264.5° to 265.5° C.

Analysis: Calc. for $C_{22}H_{28}ClNO_3S$: $0.25H_2O$: C 61.94; H 6.74; N 3.28; Cl 8.30; S 7.52. Found: C 62.26; H 6.76; N 3.23; Cl 8.17; S 7.42.

An aqueous solution of this compound has an absorption maximum at 390 nm with an E (1%; 1 cm) of 111.

EXAMPLE 7

Evaluation of the Efficiency of the Compounds given in Examples 1 to 6 as Water Soluble Photoinitiators Each of the compounds described in the previous examples was investigated as follows. A sample (0.33 g) was dissolved in water (0.8 mls) and N,N-dimethylaminoethanol (0.7 mls) added. This solution was stirred into "Azocol S" (Trade Mark) emulsion (30 g) and then N,N'-methylenebisacrylamide (1 g) added. After stirring for five minutes the mixture was allowed to stand for 16 hours prior to coating into orange polyester screen (110 threads/cm) with two coats on the direct side and one on the reverse. The coated screen was air dried and then irradiated by light which had passed first through a piece of plate glass (5 mm thick) and second through a film containing a positive image. The screen, film and glass in the form of a tight sandwich sat directly below two 375 watt photographic lamps whose bottom surfaces were positioned at a distance of 35 cms from the top surface of the piece of glass. After irradiating for a given time period the screens were gently rinsed with running cold water until an image began to form and then such treatment continued for a further two minutes. The screens were then air dried and the stencils examined. By using stepwise increasing exposure times the minimum time needed to give a good quality stencil was determined and these times are reproduced in the table below. For comparison a standard sensitized "Azocol S" emulsion was prepared according to the manufacturers instructions and after processing as described above its minimum exposure time was determined. Also the sodium salt of 2-(3-sulphopropoxy)-thioxanthone (Example 2 of EP-A-81280) was tested as above (comparative A) for comparison purposes.

| Results | |
|---|---|
| Compound of Example No. | Exposure Time in Seconds |
| 1 | 4 |
| 2 | 2 |
| 3 | 8 |
| 4 | 2 |
| 5 | 4 |
| 6 | 8 |
| Standard Compound | 30 |
| Comparative A | 8 |

These results prove the efficiency of the compounds of the present invention as water soluble photoinitiators.

"Azocol S" emulsion is a partially hydrolysed polyvinyl acetate emulsion in water. The recommended photosensitiser provided is a diazonium salt of paraphenylene diamine/formaldehyde cross-linked polymer.

We claim:

1. A thioxanthone derivative of general formula

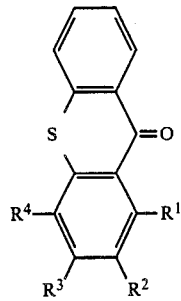

wherein one of $R^2$, $R^3$ and $R^4$ is a group of formula

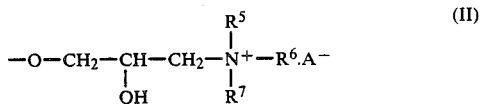

in which one of $R^5$, $R^6$ and $R^7$ is a $C_{1-20}$ alkyl or a benzyl group, the others being $C_{1-6}$ alkyl groups and $A^-$ represents an anion, and $R^1$ and the others of $R^2$, $R^3$, and $R^4$ are independently selected from hydrogen atoms, $C_{1-6}$ alkyl groups and $C_{1-6}$ alkoxy groups.

2. A derivative according to claim 1 wherein $R^1$ and said others of $R^2$, $R^3$ and $R^4$ are independently selected from hydrogen atoms and methyl groups.

3. A derivative according to claim 1 or 2 wherein $R^5$, $R^6$ and $R^7$ are all methyl groups.

4. A derivative according to claim 3 wherein A represents a chlorine or bromine atom.

5. A derivative according to claim 4 wherein $R^2$ or $R^4$ represents the group of formula II.

* * * * *